(12) United States Patent
Fautz

(10) Patent No.: US 9,615,769 B2
(45) Date of Patent: Apr. 11, 2017

(54) METHOD TO GENERATE AN RF EXCITATION PULSE TO EXCITE AN ARBITRARILY SHAPED VOLUME, METHOD FOR TARGETED EXCITATION OF SPINS WITHIN A VESSEL, AND METHOD TO CREATE MR ANGIOGRAPHY IMAGES, AND MAGNETIC RESONANCE SYSTEM

(71) Applicant: Hans-Peter Fautz, Forchheim (DE)

(72) Inventor: Hans-Peter Fautz, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 650 days.

(21) Appl. No.: 14/099,034

(22) Filed: Dec. 6, 2013

(65) Prior Publication Data

US 2014/0159722 A1    Jun. 12, 2014

(30) Foreign Application Priority Data

Dec. 6, 2012 (DE) .................. 10 2012 222 413

(51) Int. Cl.
*G01R 33/48* (2006.01)
*A61B 5/00* (2006.01)
(Continued)

(52) U.S. Cl.
CPC .............. *A61B 5/055* (2013.01); *A61B 5/004* (2013.01); *G01R 33/48* (2013.01);
(Continued)

(58) Field of Classification Search
CPC  G01R 33/48; G01R 33/4836; G01R 33/5635; G01R 33/56366; A61B 5/055; A61B 5/004
See application file for complete search history.

(56) References Cited

U.S. PATENT DOCUMENTS 5,842,989 A    12/1998  Zur
8,150,130 B2    4/2012  Kirsch
(Continued)

OTHER PUBLICATIONS

Principle, Techniques, and Application of T2 Based MR Imaging and Its Special Application (Chavhan et al).*
(Continued)

*Primary Examiner* — Clayton E Laballe
*Assistant Examiner* — Ruifeng Pu
(74) *Attorney, Agent, or Firm* — Schiff Hardin LLP

(57) ABSTRACT

In order to generate an RF excitation pulse together with a gradient curve to excite nuclear spins an arbitrarily shaped volume with a magnetic resonance system, a volume segment is prepared in which the volume is situated, such that only spins within the volume yield an MR signal portion in the subsequent detection of an MR signal. An MR signal is detected from the volume segment along a trajectory of k-space. At least one gradient for scanning k-space along the trajectory is switched during the detection. The RF excitation pulse is generated corresponding to the MR signal detected in a temporally inverted manner, and the gradient curve is generated corresponding to the temporally inverted curve of the at least one gradient to scan k-space.

22 Claims, 2 Drawing Sheets

(51) Int. Cl.
  *A61B 5/055* (2006.01)
  *G01R 33/483* (2006.01)
  *G01R 33/563* (2006.01)

(52) U.S. Cl.
  CPC ...... *G01R 33/4836* (2013.01); *G01R 33/5635* (2013.01); *G01R 33/56366* (2013.01)

(56) References Cited

U.S. PATENT DOCUMENTS

| | | |
|---|---|---|
| 2002/0036498 A1 | 3/2002 | Uetake et al. |
| 2002/0036500 A1 | 3/2002 | Uetake et al. |
| 2005/0215881 A1 | 9/2005 | Van Zijl et al. |
| 2010/0280357 A1 | 11/2010 | Bi et al. |
| 2012/0249138 A1 | 10/2012 | Pfeuffer |
| 2012/0271158 A1 | 10/2012 | Schmitt |
| 2015/0042330 A1 | 2/2015 | Gumbrecht et al. |

OTHER PUBLICATIONS

Vahedipour et al., "Direct Method for Parallel Transmit Pulse Design by Time-Reversal of the Small-Tip Angle Excitation", Proc. Intl. Soc. Mag. Reson. Med. 20 (2012), p. 637.

Stöcker et al., "Revisiting RF Feedback Pulses: Encoding Image Contrast During Excitation", Proc. Intl. Soc. Mag. Reason. Med. 20 (2012), p. 639.

Schneider et al., "Selective Labeling of Moving Spins Using Parallel 3D Spatially Selective Excitation", Proc. Intl. Soc. Mag. Reson. Med. 20 (2012), p. 640.

* cited by examiner

METHOD TO GENERATE AN RF EXCITATION PULSE TO EXCITE AN ARBITRARILY SHAPED VOLUME, METHOD FOR TARGETED EXCITATION OF SPINS WITHIN A VESSEL, AND METHOD TO CREATE MR ANGIOGRAPHY IMAGES, AND MAGNETIC RESONANCE SYSTEM

BACKGROUND OF THE INVENTION

Field of the Invention

The present invention concerns a method in order to generate an RF excitation pulse with which an arbitrarily shaped volume can excited for obtaining magnetic resonance (MR) signals. Moreover, the present invention concerns a method with which only the nuclear spins within a predetermined vessel can be specifically excited. The present invention also concerns a method in order to create MR angiography images with the use of the initial methods, as well as corresponding magnetic resonance systems to execute the method according to the invention.

Description of the Prior Art

In vascular-specific MR angiography, and in MR perfusion measurements, the nuclear spins in one or more blood vessels (in particular arteries) are specifically excited or saturated, which is also designated as "labeling". The movement of these spins due to flow or perfusion within the tissue can subsequently be tracked. For this purpose, the excitation volume that is excited by the RF excitation pulse is selected so that only the vessel of interest (and no other vessel) lies within the excitation volume. Ideally, the RF excitation pulse is selected such that it excites only the vessel of interest (and not the areas around the area of interest). For this purpose, according to the prior art selective RF excitation pulses are used, for which excitation with multiple RF antennas can be advantageous.

In "Selective Labeling of Moving Spins using Parallel 3D Spatially Selective Excitation", J. T. Schneider et al., Proc. Intl. Soc. Reson. Med. 20, 2012, Page 640, it is described how the spins in a vessel in three-dimensional space can be specifically excited with multiple RF antennas.

According to the prior art, the following two objects must be achieved for targeted excitation of a vessel:

The spatial position and the spatial dimensions of the vessel must be determined.

An RF excitation pulse must be calculated which excites only the spins within the vessel.

SUMMARY OF THE INVENTION

An object of the present invention is to simplify the generation of an RF excitation pulse for targeted excitation of a vessel in order in particular to create MR angiography images.

Within the scope of the present invention, a method is provided to generate an RF excitation pulse (or multiple RF excitation pulses) together with a magnetic field gradient curve in order to therefore excite (only) an arbitrarily shaped volume with a magnetic resonance system. This method includes the following steps:

Prepare a volume segment in which the volume is arranged so that essentially only spins within the volume (and not outside of the volume) deliver an MR signal portion in the following steps in which MR signals are acquired. For example, the spins in a flowing medium can be prepared (saturated, for example) in the volume segment) such that these spins differ from those spins that flow "fresh" into the volume, and therefore into the volume segment. This preparation step accordingly ensures that (nearly) exclusively MR signals that originate in the volume are detected in the subsequent step.

An MR signal from the volume segment is detected and entered into k-space along a trajectory of k-space. For this purpose, one or more magnetic field gradients are switched (activated) during the detection of the MR signals in order to scan (enter data into) k-space along this trajectory. Because the volume segment is arranged and prepared so that only fresh spins flowing into the volume deliver an MR signal portion, in this step only MR signals of spins within the volume are detected.

The RF excitation pulse for targeted excitation of the volume is now generated by temporally inverting (i.e., reversing the signal curve with respect to the time axis) the detected MR signal. The sought magnetic field gradient curve (that is radiated together with the RF excitation pulse for targeted excitation of the volume) corresponds to the temporally inverted curve of the magnetic field gradient or magnetic field gradients that were used to scan k-space along the trajectory.

According to the invention, the reciprocity principle between excitation and reception of an MR signal is used in order to generate the RF excitation pulse for targeted excitation of an arbitrarily shaped volume. According to this reciprocity principle, a detected MR signal that has a predetermined spatial distribution (meaning that only the spins of a defined volume deliver this MR signal) and which is acquired with a defined k-space trajectory can be used in a temporally inverted form an RF excitation pulse in order to excite the same spatial structure which has the detected MR signal (i.e. in order to excite only the spins within the volume) even if the gradients radiated simultaneously with the RF excitation pulse are time-inverted in comparison to the gradients to scan k-space.

For example, this reciprocity principle is described in "Direct method for parallel transmit pulse design by time-reversal of the small-tip angle excitation", K. Vahedipour et al., Proc. Intl. Soc. Reson. Med. 20, 2012, Page 637, and in "Revisitting [sic] RF Feedback Pulses: Encoding Image Contrast during Excitation", T. Stocker et al., Proc. Intl. Soc. Reson. Med. 20, 2012, Page 639. In these publication the MR signal, which is the basis for generation of the RF excitation pulse, is created via simulation.

In the present invention, it is to be noted that the detected MR signal is radiated in temporally inverted form (meaning the last acquired MR signal portion first or in a temporally reverse order) as an RF excitation pulse. Moreover, during the radiation of the RF excitation pulse the magnetic field gradients must be switched such that the curve of the respective magnetic field gradients corresponds to the temporally inverted curve of the corresponding magnetic field gradients with which k-space has been scanned in the acquisition of the MR signal.

The present invention offers the advantage that the RF excitation pulse exciting only the volume can be determined automatically without the exact spatial position and extent of this volume (of a blood vessel, for example) needing to be known beforehand. For example, it is advantageously sufficient to only roughly know the position of the vessel to be examined. In spite of this, the RF excitation pulse generated according to the invention will exactly excite only this vessel since it is generated based on MR signals that are emitted only from this vessel. The generation of the sought RF excitation pulse is therefore also not so time-intensive as is the case today according to the prior art.

Moreover, in comparison to the prior art fewer artifacts are also generated by the procedure according to the invention. Since a very similar magnetic field gradient curve (only temporally reversed or inverted) as is used later in the radiation of the RF excitation pulse for targeted excitation of the volume is used to scan k-space to detect the MR signal from which the RF excitation pulse is then derived, it can be assumed that the two magnetic field gradient curves (upon scanning of k-space and upon radiation of the RF excitation pulse) are nearly identical (this hardware is controlled twice in the same manner). In contrast to this, if a previously calculated magnetic field gradient curve must be switched in the radiation of the RF excitation pulse in the prior art, due to hardware inadequacies this always leads to a deviation between the calculated magnetic field gradient curve and the magnetic field gradient curve finally generated by the magnetic resonance system, which disadvantageously leads to artifacts.

The RF excitation pulse to be generated can be used for targeted excitation of an arbitrary three-dimensional volume or a two-dimensional volume (of a defined region in a slice). As used herein the "targeted excitation of a volume" is the (nearly) exclusive excitation of this volume, while regions outside of the volume are (nearly) not excited.

As has already been indicated in the preceding, the preparation of the volume segment can include a saturation or inversion of the spins in the volume segment. In the detection of the MR signal, only MR signal portions from fresh spins flowing into the volume (and therefore unsaturated or, respectively, uninverted spins) are still detected.

This preparation and subsequent detection of the MR signal can be equated with the creation of an angiography exposure, for example of an angiography image of a TOF ("Time of Flight") angiography.

The RF excitation pulse normally has a flip angle which is less than 30°.

It is also possible for the RF excitation pulse to have a flip angle that is 30° or greater. In this case, however, the RF excitation pulse must be adapted or varied depending on the magnitude of the flip angle and depending on the detected MR signal so that the correspondingly adapted RF excitation pulse excites only the volume.

According to the invention, the MR signal is detected by an RF antenna from which the RF excitation pulse is then also radiated. However, it is also possible that MR signal is detected simultaneously with multiple RF antennas. In this case, the selective RF excitation pulse to be generated is also radiated simultaneously by these multiple RF antennas. The curve of the RF excitation pulse that is radiated by the respective RF antenna corresponds to the temporally inverted curve of the MR signal that has been detected by the respective RF antenna in the scanning of k-space along the trajectory. The magnetic field gradient curve that was switched to scan k-space is in turn switched in a temporally inverted form in the radiation of the RF excitation pulse with the multiple RF antennas.

In comparison to the use of only one RF antenna, the use of multiple RF antennas or multiple channels in the generation of the RF excitation pulse has the advantage that the duration during which the RF excitation pulse is radiated can be kept shorter given the use of multiple RF antennas than if the RF excitation pulse is radiated by only one RF antenna.

In a preferred embodiment according to the invention, the step of preparing the volume segment also includes a determination of the volume segment. The volume segment is determined such that, outside of the volume, said volume segment comprises no additional volume which has properties comparable to the volume.

Expressed differently, the volume segment is determined so that—for example among multiple similar volumes (vessels, for example) only the desired volume (for example the desired vessel) lies within the volume segment. For example, if a defined blood vessel should be specifically excited with the RF excitation pulse to be generated, in proximity to which specific blood vessel is located an additional, similarly large blood vessel, then the volume segment is selected so that only that specific blood vessel and not the additional blood vessel as well lies within the volume segment. If the volume segment is a two-dimensional slice, this slice can (for example) be selected (thus flipped) so that only the desired volume or vessel lies within this slice.

It is noted that, according to the invention, it is also possible to excite not only one volume but multiple volumes with the same RF excitation pulse. In order to excite multiple volumes (within the volume segment) with the same RF excitation pulse, it must be ensured that (only) MR signal portions from all of these volumes are detected in the acquisition of the MR signal.

Within the scope of the present invention, a method is also provided for targeted excitation of spins within a vessel with a magnetic resonance system. This vessel thereby corresponds to the arbitrarily shaped volume, and the RF excitation pulse is generated together with the necessary magnetic field gradient curve according to the method according to the invention that is described in the preceding for the generation of an RF excitation pulse.

Moreover, within the scope of the present invention a method is provided to create MR angiography images of a predetermined volume segment of a living examination subject with the aid of a magnetic resonance system. This method includes the following steps:

Only the spins in a vessel within the volume segment are specifically excited with the aid of the method according to the invention that is described in the preceding for the targeted excitation of spins.

MR data from the volume segment are acquired via a corresponding scanning of k-space after the spins in the vessel have been excited.

The MR angiography images of the volume segment are generated from these MR data acquired in such a manner.

It is noted that, in both the method according to the invention for the targeted excitation of spins within one or more vessels and in the method according to the invention to create MR angiography images, what is known as the pTX technology can be used in which the RF excitation is generated with multiple RF antennas operating in parallel.

Within the scope of the present invention, a magnetic resonance system is also provided to generate an RF excitation pulse together with a magnetic field gradient curve to excite an arbitrarily shaped volume. The magnetic resonance system has a basic field magnet, a gradient field system, at least one transmission/reception antenna, at least one reception coil element, and a control device. The control device serves to control the gradient field system and the at least one RF transmission/reception antenna. Moreover, the control device is designed in order to receive measurement signals which have been detected by the at least one RF transmission/reception antenna or by the at least one reception coil element. The magnetic resonance system is designed in order to prepare a volume segment in which the volume is arranged so that an MR signal portion is delivered only by spins within the volume given a following acquisition of an MR signal. Moreover, the magnetic resonance system is designed in order to detect the MR signal from the volume segment along a trajectory of k-space while the magnetic resonance system simultaneously switches one or more gradients in order to scan k-space along the trajectory. The control device is designed in order to generate the RF excitation pulse which corresponds to the MR signal acquired in a temporally inverted manner, and the magnetic field gradient curve which corresponds to the temporally inverted curve of the gradient or gradients to scan k-space.

The advantages of the magnetic resonance system according to the invention essentially correspond to the advantages of the method according to the invention which have been described in detail above.

The present invention also encompasses a non-transitory, computer-readable data storage medium encoded with programming instructions that, when the storage medium is loaded into a computerized control system of a magnetic resonance imaging apparatus, cause the control system to operate the magnetic resonance imaging apparatus by executing one or more of the above-described embodiments of the method according to the invention.

The programming instructions can be a source code (C++, for example) that must still be compiled and linked or that must only be interpreted, or an executable software code that is only to be loaded into the corresponding computer or, respectively, control device for execution.

The electronically readable data medium can be, for example a DVD, a magnetic tape or a USB stick, on which is stored electronically readable control information.

The present invention is in particular suitable for vessel-specific MR angiography or MR perfusion measurement. Naturally, however, the present invention is not limited to this preferred field of application since the present invention can, for example, also be used in order to generate an RF excitation pulse for an arbitrarily shaped volume without this RF excitation pulse subsequently being used for angiography or perfusion measurement.

DESCRIPTION OF THE PREFERRED EMBODIMENTS

Figure 1:
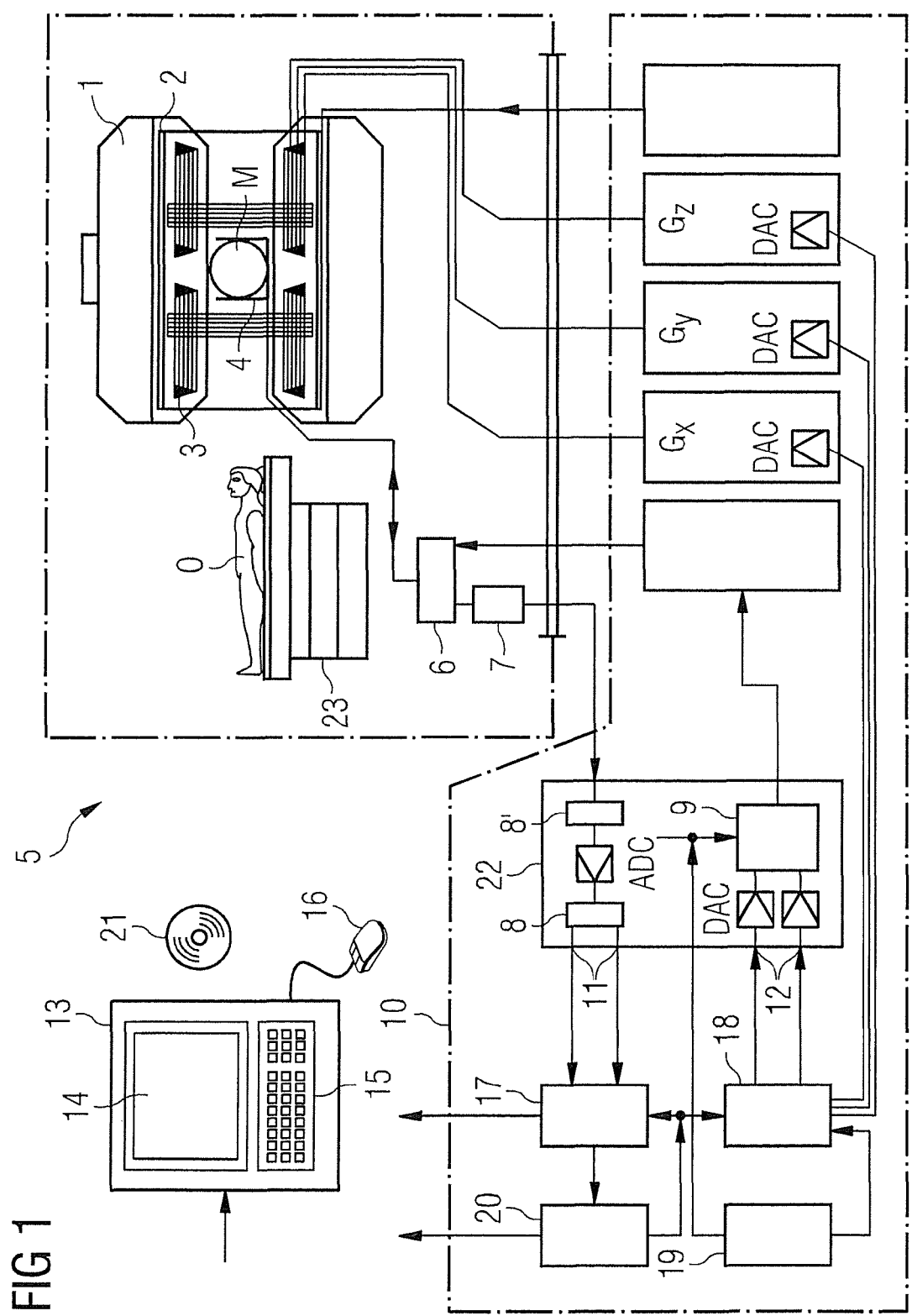
FIG. 1 schematically illustrates a magnetic resonance system according to the invention.

FIG. 1 shows a schematic representation of a magnetic resonance system 5 (a magnetic resonance imaging or magnetic resonance tomography apparatus). A basic field magnet 1 generates a temporally constant, strong magnetic field for polarization or alignment of the nuclear spins in a volume segment of a subject O (for example a part of a human body that is to be examined) which, lying on a table 23, and is examined in the magnetic resonance system 5. The high homogeneity of the basic magnetic field that is required for the nuclear magnetic resonance measurement is defined in a typically spherical measurement volume M in which the parts of the human body that are to be examined are arranged. To support the homogeneity requirements, and in particular to eliminate temporally invariable influences, shim plates made of ferromagnetic material are mounted at a suitable location. Temporally variable influences are eliminated by shim coils 2.

In the basic field magnet 1, a cylindrical gradient coil system 3 is used that has three sub-windings. Each sub-winding is supplied by an amplifier with current to generate a linear (also temporally variable) gradient field in the respective direction of the Cartesian coordinate system. The first sub-winding of the gradient field system 3 generates a gradient $G_x$ in the x-direction, the second sub-winding generates a gradient $G_y$ in the y-direction, and the third sub-winding generates a gradient $G_z$ in the z-direction. Each amplifier has a digital/analog converter that is controlled by a sequence controller 18 for time-accurate generation of gradient pulses.

Located within the gradient field system 3 is one or more radio-frequency antennas 4 which convert the radio-frequency pulses emitted by a radio-frequency power amplifier into an alternating magnetic field for excitation of the nuclei and alignment of the nuclear spins of the subject O to be examined or of the region of the subject O that is to be examined, or which also detect an MR signal. Each radio-frequency antenna 4 has one or more RF transmission coils and one or more RF reception coils in the form of an annular (advantageously linear or matrix-like) arrangement of component coils. The alternating field emanating from the processing nuclear spins—i.e. normally the nuclear spin echo signals caused by a pulse sequence made up of one or more radio-frequency pulses and one or more gradient pulses—is also converted by the RF reception coils of the respective radio-frequency antenna 4 into a voltage (measurement signal) which is supplied via an amplifier 7 to a radio-frequency reception channel 8 of a radio-frequency system 22. The radio-frequency system 22 (which is part of a control device 10 of the magnetic resonance system 5) furthermore has a transmission channel 9 in which the radio-frequency pulses are generated for the excitation of the nuclear magnetic resonance. The respective radio-frequency pulses are digitally represented in the sequence controller 18 as a series of complex numbers based on a pulse sequence predetermined by the system computer 20. This number sequence is supplied as a real part and imaginary part to a digital/analog converter in the radio-frequency system 22 via respective inputs 12, and from the digital/analog converter to a transmission channel 9. In the transmission channel 9, the pulse sequences are modulated on a radio-frequency carrier signal whose base frequency corresponds to the center frequency.

The switching from transmission operation to reception operation takes place via a transmission/reception diplexer 6. The RF transmission coils of the radio-frequency antenna(s) 4 radiate(s) the radio-frequency pulses for excitation of the nuclear spins into the measurement volume M and scans resulting echo signals via the RF reception coil(s). The correspondingly acquired magnetic resonance signals are phase-sensitively demodulated to an intermediate frequency in a reception channel 8' (first demodulator) of the radio-frequency system 22 and digitized in an analog/digital converter (ADC). This signal is further demodulated to a frequency of 0. The demodulation to a frequency of 0 and the separation into real part and imaginary part occur in a second reception channel 8 (second demodulator) after the digitization in the digital domain. An MR image or three-dimensional image data set is reconstructed by an image computer 17 from the measurement data acquired in such a manner. The administration of the measurement data, the image data and the control programs takes place via the system computer 20. Based on a specification with control programs, the sequence controller 18 monitors the generation of the respective desired pulse sequences and the corresponding scanning of k-space. In particular, the sequence controller 18 controls the time-accurate switching of the gradients, the emission of the radio-frequency pulses with defined phase amplitude and the reception of the nuclear magnetic resonance signals. The time base for the radio-frequency system 22 and the sequence controller 18 is provided by a synthesizer 19. The selection of corresponding control programs to generate an MR angiography image (which control programs are stored on a DVD 21, for example) and the presentation of the generated MR image take place via a terminal 13 which comprises a keyboard 15, a mouse 16 and a monitor 14.

Figure 2:
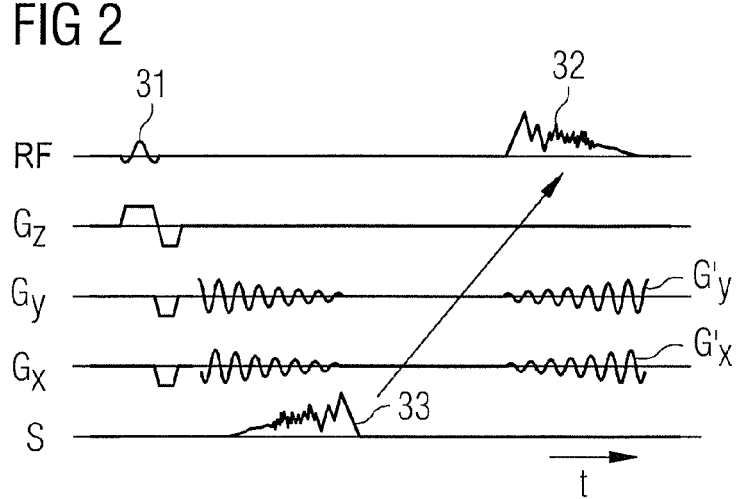
FIG. 2 is a sequence diagram showing how an RE excitation pulse for targeted excitation of a vessel is created according to the invention.

In the form of a sequence diagram, FIG. 2 shows how an RF excitation pulse 32 for targeted excitation of a vessel is generated according to the invention.

In a first step, a predetermined volume segment 34 in which the vessel 35 is situated is prepared as explained in more detail in the following with FIG. 3. An RF pulse 31 is then radiated while gradients Gx-Gz are switched, so the volume segment is excited (i.e., nuclear spins in the volume segment are excited). The MR signal 33 is subsequently detected from the volume segment 34 by entering MR data into k (i.e., scanning k-space) along a trajectory. The path of the trajectory is determined by the gradients Gx, Gy that are switched (activated) during the detection of the MR signal 33.

The sought RF excitation pulse 32 corresponds in a time-inverted form of the detected MR signal 33 as is presented in the following Equation (1).

$$RF(t)=s(T-t) \quad (1)$$

wherein RF(t) is the time curve of the RF excitation pulse 32, and s(t) is the time curve of the detected MR signal 33. T is the duration during which k-space is scanned, or the MR signal 33 is detected, and during which the RF excitation pulse is to be radiated later for selective excitation of the vessel 35.

While the RF excitation pulse 32 is being radiated in order to specifically excite only the spins within the vessel, the gradients Gx', Gy' are switched, which correspond in a time-inverted form of the gradients Gx, Gy that were switched to scan k-space.

The time curve of the gradient Gx' of the following Equation (2) accordingly obeys the following Equation (2) while the time curve of the gradient Gy' satisfies Equation (3).

$$Gx'(t)=Gx(T-t) \quad (2)$$

$$Gy'(t)=Gy(T-t) \quad (3)$$

Figure 3:
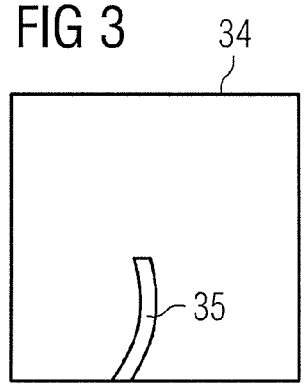
FIG. 3 schematically illustrates a predetermined volume segment with a volume to be excited.

The predetermined volume segment 34 and the vessel 35 to be excited (which lies within the predetermined volume segment 34) are schematically depicted in FIG. 3.

The spins within the predetermined volume segment 34 are saturated or inverted to generate the sought RF excitation pulse 32. When the volume segment 34 is subsequently excited and the MR signal 33 is detected from the volume segment 34, this MR signal 33 is generated from spins which have freshly flowed into the volume segment 34, or into the vessel 35. The generation and subsequent detection of the MR signal 33 from the vessel 35 corresponds to the procedure in an MR angiography measurement.

Figure 4:
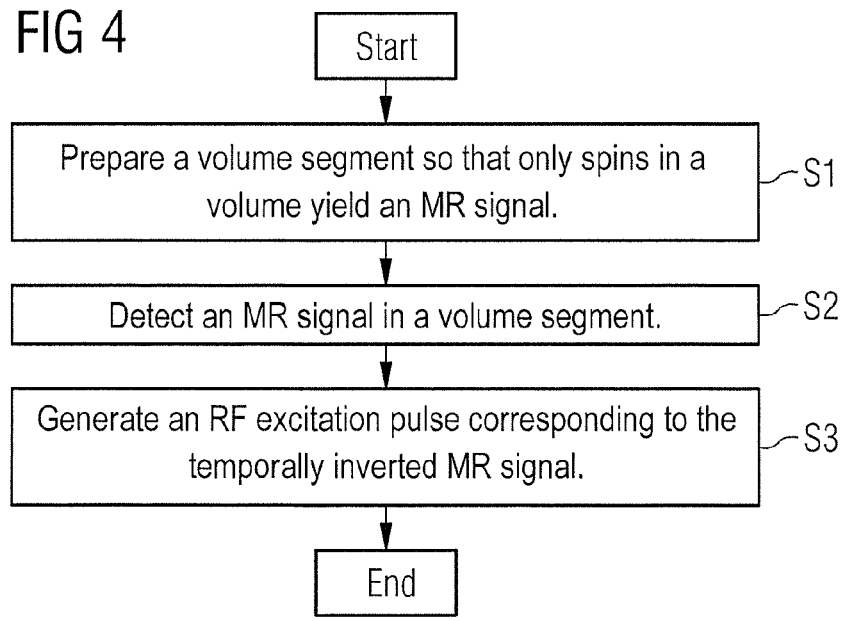
FIG. 4 is a flowchart of a method according to the invention for the generation of an RF excitation pulse.

A flowchart of an embodiment of the method according to the invention is shown in FIG. 4.

In a first Step S1, the volume segment 34 is prepared such that only spins in a volume or vessel 35 yield an MR signal portion in a subsequent measurement. For example, this preparation can be implemented in that the spins of the volume segment 34 are saturated or inverted with the magnetic resonance system 5.

In the following Step S2, the MR signal 33 is detected from the volume segment 34 in that k-space is scanned along a predetermined trajectory. In the following Step S3, the RF excitation pulse 32 is generated based on this MR signal 33 such that it corresponds to a temporally inverted MR signal 33.

Due to the reciprocity principle between excitation and reception of an MR signal, the radiation of the RF excitation pulse 32 generated in such a manner excites only the spins within the vessel 35 if at the same time the gradients Gx', Gy' are switched which correspond to a temporal inversion of the gradients Gx, Gy that were used to scan k-space along the trajectory.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to generate a radio-frequency (RF) excitation pulse together with a gradient curve for a targeted excitation of nuclear spins in an arbitrarily shaped volume, comprising:

from a computerized control unit, operating a magnetic resonance (MR) data acquisition unit in which an examination volume is situated, to prepare a volume segment in said volume to cause only nuclear spins within said volume to contribute to an MR signal in a subsequent detection of said magnetic resonance signal;

from said control unit, operating said MR data acquisition unit to detect said MR signal from said volume segment while activating at least one gradient that causes data representing the detected magnetic resonance signal to be entered into an electronic memory organized as k-space, along a trajectory in k-space defined by said at least one gradient, said MR signal having an MR signal curve with respect to time and said at least one gradient having a gradient curve with respect to time; and in said control unit, automatically generating said RF excitation pulse for said targeted excitation as an RF pulse having an RF pulse curve that is a temporal inversion of said MR signal curve, and generating said gradient curve for said targeted excitation as a gradient having a gradient curve that is a temporal inversion of the gradient curve of said at least one gradient activated during detection of said MR signal, and making an electronic signal available at an output of said control unit embodying said RF excitation pulse and said gradient curve for said targeted excitation in a form usable to operate said MR data acquisition unit to implement said targeted excitation.

2. A method as claimed in claim 1 comprising:

preparing said volume by saturating or inverting said nuclear spins in said volume segment; and detecting said MR signal by detecting MR signal contributions produced by nuclear spins in a flowing medium that have flowed into said volume after preparing said volume segment.

3. A method as claimed in claim 1 comprising generating said RF excitation pulse for said targeted excitation with a flip angle that is less than 30°.

4. A method as claimed in claim 1 comprising:
generating said RF excitation pulse for said targeted excitation with a flip angle that is greater than or equal to 30°; and
in said control unit, adapting said RF excitation pulse for said targeted excitation dependent on a magnitude of said flip angle and dependent on the detected MR signal in order to excite only nuclear spins in said volume.

5. A method as claimed in claim 1 wherein said MR data acquisition unit comprises multiple RF antennas, and wherein said method comprises:
detecting said MR signal with each of said RF antennas, thereby resulting in a plurality of respectively detected MR signals; and
in said control unit, generating said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna.

6. A method as claimed in claim 1 comprising:
in said control unit, determining said volume segment such that, outside of said volume, said volume segment comprises no additional volume having properties comparable to properties of said volume.

7. A method for targeted excitation of nuclear spins within a blood vessel, comprising:
from a computerized control unit, operating a magnetic resonance (MR) data acquisition unit in which an examination volume is situated, to prepare a volume segment in said volume to cause only nuclear spins within said volume to contribute to an MR signal in a subsequent detection of said MR signal;
from said control unit, operating said MR data acquisition unit to detect said MR signal from said volume segment while activating at least one gradient that causes data representing the detected MR signal to be entered into an electronic memory organized as k-space, along a trajectory in k-space defined by said at least one gradient, said MR signal having an MR signal curve with respect to time and said at least one gradient having a gradient curve with respect to time;
in said control unit, automatically generating said RF excitation pulse for said targeted excitation as an RF pulse having an RF pulse curve that is a temporal inversion of said MR signal curve, and generating said gradient curve for said targeted excitation as a gradient having a gradient curve that is a temporal inversion of the gradient curve of said at least one gradient activated during detection of said MR signal; and
from said control unit operating said MR data acquisition unit to implement said targeted excitation by radiating said RF excitation pulse and activating said gradient curve.

8. A method as claimed in claim 7 wherein said MR data acquisition unit comprises multiple RF antennas, and wherein said method comprises:
detecting said MR signal with each of said RF antennas, thereby resulting in a plurality of respectively detected MR signals;
in said control unit, generating said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna; and
radiating said plurality of RF pulses respectively from said multiple of RF antennas in said targeted excitation.

9. A method to generate a magnetic resonance (MR) angiography image of an examination subject, comprising:
from a computerized control unit, operating an MR data acquisition unit in which an examination volume is situated, to prepare a vessel in said volume to cause only nuclear spins within said vessel to contribute to an MR signal in a subsequent detection of said MR signal;
from said control unit, operating said MR data acquisition unit to detect said MR signal from said vessel while activating at least one gradient that causes data representing the detected MR signal to be entered into an electronic memory organized as k-space, along a trajectory in k-space defined by said at least one gradient, said MR signal having an MR signal curve with respect to time and said at least one gradient having a gradient curve with respect to time; and
in said control unit, automatically generating said RF excitation pulse for a subsequent targeted excitation of said vessel as an RF pulse having an RF pulse curve that is a temporal inversion of said MR signal curve, and generating said gradient curve for said targeted excitation of said vessel as a gradient having a gradient curve that is a temporal inversion of the gradient curve of said at least one gradient activated during detection of said MR signal;
from said control unit, operating said MR data acquisition unit by radiating said RF excitation pulse and activating said gradient curve to implement said targeted excitation of said vessel, and acquiring MR data following said targeted excitation; and
in a processor, reconstructing an angiographic image of said vessel from said MR data acquired following said targeted excitation.

10. A method as claimed in claim 9 wherein said MR data acquisition unit comprises multiple RF antennas, and wherein said method comprises:
detecting said MR signal with each of said RF antennas, thereby resulting in a plurality of respectively detected MR signals; and
in said control unit, generating said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna.

11. A magnetic resonance (MR) apparatus a radio-frequency (RF) excitation pulse together with a gradient curve for a targeted excitation of nuclear spins in an arbitrarily shaped volume, comprising:
an MR data acquisition unit;
a computerized control unit configured to operate the MR data acquisition unit in which an examination volume is situated, to prepare a volume segment in said volume to cause only nuclear spins within said volume to contribute to an MR signal in a subsequent detection of said magnetic resonance signal;
said control unit being configured to operate said MR data acquisition unit to detect said MR signal from said volume segment while activating at least one gradient that causes data representing the detected magnetic resonance signal to be entered into an electronic memory organized as k-space, along a trajectory in k-space defined by said at least one gradient, said MR signal having an MR signal curve with respect to time and said at least one gradient having a gradient curve with respect to time; and said control unit being configured to automatically generate said RF excitation pulse for said targeted excitation as an RF pulse having an RF pulse curve that is a temporal inversion of said MR signal curve, and to generate said gradient curve for said targeted excitation as a gradient having a gradient curve that is a temporal inversion of the gradient curve of said at least one gradient activated during detection of said MR signal, and to make an electronic signal available at an output of said control unit embodying said RF excitation pulse and said gradient curve for said targeted excitation in a form usable to operate said MR data acquisition unit to implement said targeted excitation.

12. An apparatus as claimed in claim 11 wherein:
said MR data acquisition unit comprises multiple RF antennas;
said control unit is configured to operate said MR data acquisition unit to detect said MR signal with each of said RF antennas, thereby resulting in a plurality of respectively detected MR signals; and
said control unit being configured to generate said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna.

13. A magnetic resonance (MR) apparatus for targeted excitation of nuclear spins within a blood vessel, comprising:
an MR data acquisition unit;
a computerized control unit configured to operate an MR data acquisition unit in which an examination volume is situated, to prepare a volume segment in said volume to cause only nuclear spins within said volume to contribute to an MR signal in a subsequent detection of said MR signal;
said control unit being configured to operate said MR data acquisition unit to detect said MR signal from said volume segment while activating at least one gradient that causes data representing the detected MR signal to be entered into an electronic memory organized as k-space, along a trajectory in k-space defined by said at least one gradient, said MR signal having an MR signal curve with respect to time and said at least one gradient having a gradient curve with respect to time;
said control unit being configured to automatically generate said RF excitation pulse for said targeted excitation as an RF pulse having an RF pulse curve that is a temporal inversion of said MR signal curve, and to generate said gradient curve for said targeted excitation as a gradient having a gradient curve that is a temporal inversion of the gradient curve of said at least one gradient activated during detection of said MR signal; and
said control unit being configured to operate said MR data acquisition unit to implement said targeted excitation by radiating said RF excitation pulse and activating said gradient curve.

14. An apparatus as claimed in claim 13 wherein:
said MR data acquisition unit comprises multiple RF antennas;
said control unit is configured to operate said MR data acquisition unit to detect said MR signal with each of said RF antennas, thereby resulting in a plurality of respectively detected MR signals;
said control unit is configured to generate said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna; and
said control unit is configured to operate said MR data acquisition unit to radiate said plurality of RF pulses respectively from said multiple of RF antennas in said targeted excitation.

15. A magnetic resonance (MR) apparatus to generate an MR angiography image of an examination subject, comprising:
an MR data acquisition unit;
a computerized control unit configured to operate the MR data acquisition unit in which an examination volume is situated, to prepare a vessel in said volume to cause only nuclear spins within said vessel to contribute to an MR signal in a subsequent detection of said MR signal;
said control unit being configured to operate said MR data acquisition unit to detect said MR signal from said vessel while activating at least one gradient that causes data representing the detected MR signal to be entered into an electronic memory organized as k-space, along a trajectory in k-space defined by said at least one gradient, said MR signal having an MR signal curve with respect to time and said at least one gradient having a gradient curve with respect to time; and
said control unit being configured to automatically generate an RF excitation pulse for a subsequent targeted excitation of said vessel as an RF pulse having an RF pulse curve that is a temporal inversion of said MR signal curve, and to generate said gradient curve for said targeted excitation of said vessel as a gradient having a gradient curve that is a temporal inversion of the gradient curve of said at least one gradient activated during detection of said MR signal;
said control unit being configured to operate said MR data acquisition unit by radiating said RF excitation pulse and activating said gradient curve to implement said targeted excitation of said vessel, and acquiring MR data following said targeted excitation; and
a processor configured to reconstruct an angiographic image of said vessel from said MR data acquired following said targeted excitation.

16. An apparatus as claimed in claim 15 wherein:
said MR data acquisition unit comprises multiple RF antennas;
said control unit is configured to operate said MR data acquisition unit to detect said MR signal with each of said RF antennas, thereby resulting in a plurality of respectively detected MR signals; and
said control unit is configured to generate said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna.

17. A non-transitory, computer-readable data storage medium encoded with programming instructions, said storage medium being loaded into a computerized control and processing system of a magnetic resonance (MR) apparatus that also comprises an MR data acquisition unit, said programming instructions causing said computerized control and evaluation system to:
  operate the magnetic MR data acquisition unit in which an examination volume is situated, to prepare a volume segment in said volume to cause only nuclear spins within said volume to contribute to an MR signal in a subsequent detection of said magnetic resonance signal;
  operate said MR data acquisition unit to detect said MR signal from said volume segment while activating at least one gradient that causes data representing the detected magnetic resonance signal to be entered into an electronic memory organized as k-space, along a trajectory in k-space defined by said at least one gradient, said MR signal having an MR signal curve with respect to time and said at least one gradient having a gradient curve with respect to time; and
  automatically generate an RF excitation pulse for a subsequent targeted excitation of said volume as an RF pulse having an RF pulse curve that is a temporal inversion of said MR signal curve, and generate said gradient curve for said targeted excitation as a gradient having a gradient curve that is a temporal inversion of the gradient curve of said at least one gradient activated during detection of said MR signal, and make an electronic signal available at an output of said control and evaluation system embodying said RF excitation pulse and said gradient curve for said targeted excitation in a form usable to operate said MR data acquisition unit to implement said targeted excitation.

18. A non-transitory, computer-readable data storage medium as claimed in claim 17 wherein said MR data acquisition unit comprises multiple RF antennas, and wherein said programming instructions cause said control and evaluation system to:
  operate said MR data acquisition unit to detect said MR signal with each of said RF antennas, thereby resulting in a plurality of respectively detected MR signals; and
  generate said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna.

19. A non-transitory, computer-readable data storage medium encoded with programming instructions, said storage medium being loaded into a computerized control and processing system of a magnetic resonance (MR) apparatus that also comprises an MR data acquisition unit, said programming instructions causing said computerized control and evaluation system to:
  operate the MR data acquisition unit in which an examination volume is situated, to prepare a volume segment in said volume to cause only nuclear spins within said volume to contribute to an MR signal in a subsequent detection of said MR signal;
  operate said MR data acquisition unit to detect said MR signal from said volume segment while activating at least one gradient that causes data representing the detected MR signal to be entered into an electronic memory organized as k-space, along a trajectory in k-space defined by said at least one gradient, said MR signal having an MR signal curve with respect to time and said at least one gradient having a gradient curve with respect to time;
  automatically generate an RF excitation pulse for a subsequent targeted excitation of said volume as an RF pulse having an RF pulse curve that is a temporal inversion of said MR signal curve, and generating said gradient curve for said targeted excitation as a gradient having a gradient curve that is a temporal inversion of the gradient curve of said at least one gradient activated during detection of said MR signal; and
  operate said MR data acquisition unit to implement said targeted excitation by radiating said RF excitation pulse and activating said gradient curve.

20. A non-transitory, computer-readable data storage medium as claimed in claim 19 wherein said MR data acquisition unit comprises multiple RF antennas, and wherein said programming instructions cause said control and evaluation system to:
  operate said MR data acquisition unit to detect said MR signal with each of said RF antennas, thereby resulting in a plurality of respectively detected MR signals;
  generate said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna; and
  operate said MR data acquisition unit to radiate said plurality of RF pulses respectively from said multiple of RF antennas in said targeted excitation.

21. A non-transitory, computer-readable data storage medium encoded with programming instructions, said storage medium being loaded into a computerized control and processing system of a magnetic resonance (MR) apparatus that also comprises an MR data acquisition unit, said programming instructions causing said computerized control and evaluation system to:
  operate the MR data acquisition unit in which an examination volume is situated, to prepare a vessel in said volume to cause only nuclear spins within said vessel to contribute to an MR signal in a subsequent detection of said MR signal;
  operating said MR data acquisition unit to detect said MR signal from said vessel while activating at least one gradient that causes data representing the detected MR signal to be entered into an electronic memory organized as k-space, along a trajectory in k-space defined by said at least one gradient, said MR signal having an MR signal curve with respect to time and said at least one gradient having a gradient curve with respect to time; and
  automatically generate an RF excitation pulse for a subsequent targeted excitation of said vessel as an RF pulse having an RF pulse curve that is a temporal inversion of said MR signal curve, and generate said gradient curve for said targeted excitation of said vessel as a gradient having a gradient curve that is a temporal inversion of the gradient curve of said at least one gradient activated during detection of said MR signal;
  operate said MR data acquisition unit by radiating said RF excitation pulse and activating said gradient curve to implement said targeted excitation of said vessel, and acquiring MR data following said targeted excitation; and reconstruct an angiographic image of said vessel from said MR data acquired following said targeted excitation.

22. A non-transitory, computer-readable data storage medium as claimed in claim 21 wherein said MR data acquisition unit comprises multiple RF antennas, and wherein said programming instructions cause said control and evaluation system to:

operate said MR data acquisition unit to detect said MR signal with each of said RF antennas, thereby resulting in a plurality of respectively detected MR signals; and generate said RF excitation pulse for said targeted excitation as a plurality of RF pulses to be respectively radiated by said multiple RF antennas, with each RF pulse to be radiated by each RF antenna being a temporal inversion of the respective MR signal detected by the respective RF antenna.

* * * * *